(12) United States Patent
Yin et al.

(10) Patent No.: US 11,823,193 B2
(45) Date of Patent: Nov. 21, 2023

(54) SECURE TRANSACTION UTILIZING BONE CONDUCTIVE CHARACTERISTIC

(71) Applicant: INTERNATIONAL BUSINESS MACHINES CORPORATION, Armonk, NY (US)

(72) Inventors: Ting Yin, Beijing (CN); Dong Chen, Beijing (CN); Ting Ting BJ Zhan, Beijing (CN); Xiang Juan Meng, Beijing (CN); Yin Xia, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 537 days.

(21) Appl. No.: 16/029,958

(22) Filed: Jul. 9, 2018

(65) Prior Publication Data

US 2020/0013067 A1    Jan. 9, 2020

(51) Int. Cl.
*G06Q 20/40* (2012.01)
*A61B 5/053* (2021.01)

(52) U.S. Cl.
CPC ....... *G06Q 20/40145* (2013.01); *A61B 5/053* (2013.01)

(58) Field of Classification Search
CPC ..... G10L 13/027; G10L 13/02; G10L 13/033; G10L 17/005; A61B 8/0875; H04L 9/0643
See application file for complete search history.

(56) References Cited

U.S. PATENT DOCUMENTS

| 9,736,180 | B2 | 8/2017 | Baldwin et al. |
| 2004/0220807 | A9* | 11/2004 | Tamir ................ B32B 37/182 |
| | | | 704/246 |
| 2014/0050321 | A1* | 2/2014 | Albert ................ A61B 5/0026 |
| | | | 380/270 |
| 2015/0127541 | A1 | 5/2015 | Just et al. |

FOREIGN PATENT DOCUMENTS

| CN | 104219597 A | 12/2014 | |
| CN | 104424696 A | 3/2015 | |
| CN | 107147760 A | 9/2017 | |
| CN | 107453778 A | 12/2017 | |
| WO | WO-2009104437 A1 * | 8/2009 | ........... A61B 8/0875 |

OTHER PUBLICATIONS

Machine generated English translation of WO-2009104437-A1.*
Moeller, "Touch-Triggered Payment Using a Wearable Device", Technical Disclosure Commons, Jun. 2017, pp. 1-4.
McLean, "Westpac Opts for Own Wearable 'PayWear' Devices", Oct. 2017, pp. 1-5.

* cited by examiner

*Primary Examiner* — Ojo O Oyebisi
(74) *Attorney, Agent, or Firm* — Tutunjian & Bitetto, P.C.; Kurt Goudy

(57) ABSTRACT

Methods, computer program products, systems are provided for securely performing electronic transactions over a network. An acoustic wave signal is received. The acoustic wave signal is encoded with at least an identifier of a payer of a transaction and transaction information of the transaction. The identifier of the payer and the transaction information is then obtained from the acoustic wave signal. A bone conduction characteristic of the payer is retrieved based on the identifier of the payer and based on the received bone conduction characteristic of the payer, the payer is verified. Completion of the transaction is allowed based on (Continued)

the transaction information in response to the payer being verified.

13 Claims, 6 Drawing Sheets

SECURE TRANSACTION UTILIZING BONE CONDUCTIVE CHARACTERISTIC

BACKGROUND

Technical Field

The present invention generally relates to data processing, and more specifically, to methods, systems and computer program products for secure payment utilizing a bone conduction characteristic.

Description of the Related Art

Electronic payment systems can reduce the costs of exchanging goods and services, and are indispensable to the functioning of the modern society. Various standards and protocols have been developed to meet the ever-growing payment needs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment of the present invention, a computer-implemented method for securely performing electronic transactions over a network is provided. The method includes receiving, by one or more processing units, an acoustic wave signal encoded with at least an identifier of a payer of a transaction and transaction information of the transaction. The identifier of the payer and the transaction information is obtained from the acoustic wave signal. A bone conduction characteristic of the payer is retrieved based on the identifier of the payer and based on the received bone conduction characteristic of the payer, the payer is verified. Completion of the transaction is allowed based on the transaction information in response to the payer being verified.

In another illustrative embodiment of the present invention, a computer program product including a computer readable storage having a computer readable program stored therein is provided. The computer readable program, when executed on a computing device, causes the computing device to perform a method for securely performing electronic transactions over a network. The method includes receiving an acoustic wave signal encoded with at least an identifier of a payer of a transaction and transaction information of the transaction, obtaining the identifier of the payer and the transaction information from the acoustic wave signal, retrieving a bone conduction characteristic of the payer based on the identifier of the payer, verifying the payer based on the retrieved bone conduction characteristic of the payer, and allowing completion of the transaction based on the transaction information in response to the payer being verified.

In yet another illustrative embodiment of the present invention, a system for securely performing electronic transactions over a network is provided. The system includes one or more processing units, a memory coupled to the one or more processing units, and computer readable program stored in the memory. The computer readable program includes program code to receive an acoustic wave signal encoded with at least an identifier of a payer of a transaction and transaction information of the transaction, program code to obtain the identifier of the payer and the transaction information from the acoustic wave signal, program code to retrieve a bone conduction characteristic of the payer based on the identifier of the payer, program code to verify the payer based on the retrieved bone conduction characteristic of the payer, and program code to allow the completion of the transaction based on the transaction information in response to the payer being verified.

These and other features and advantages of the present invention will be described in, or will become apparent to those of ordinary skill in the art in view of, the following detailed description of the example embodiments of the present invention.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Figure 1:
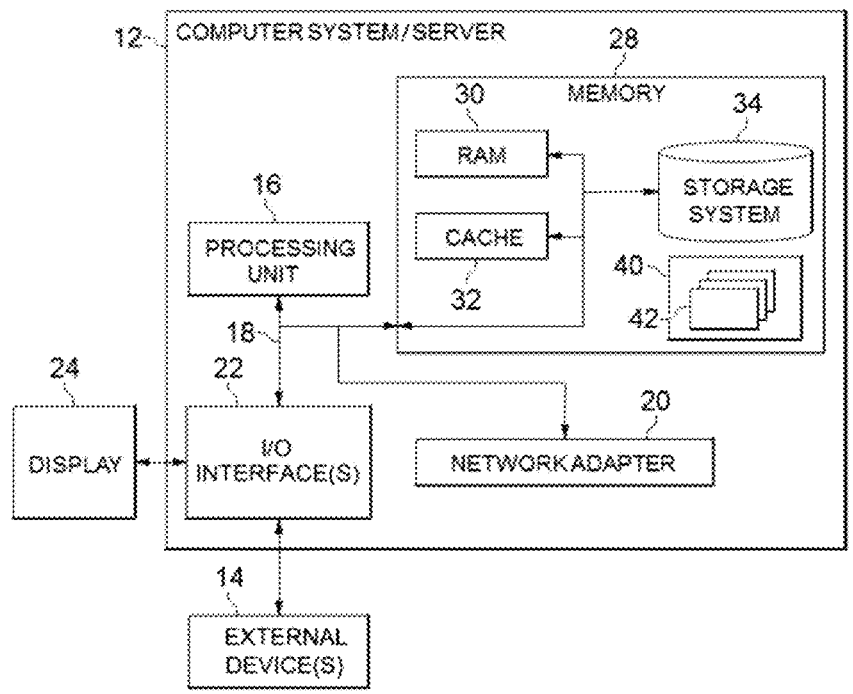
FIG. 1 depicts a cloud computing node according to an embodiment of the present invention.

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein.

Embodiments of the invention can be deployed on cloud computer systems which will be described in the following. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristic, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
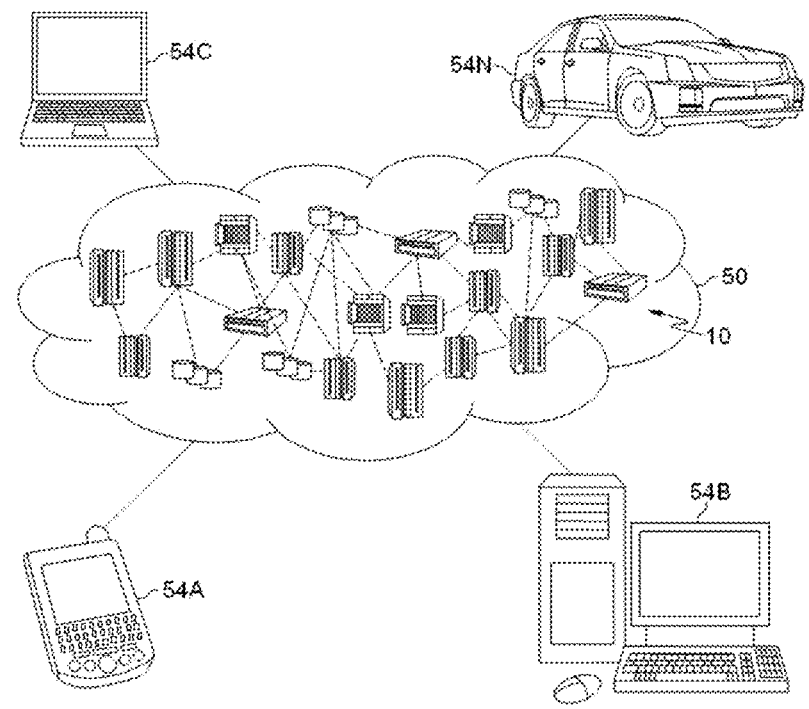
FIG. 2 depicts a cloud computing environment according to an embodiment of the present invention.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
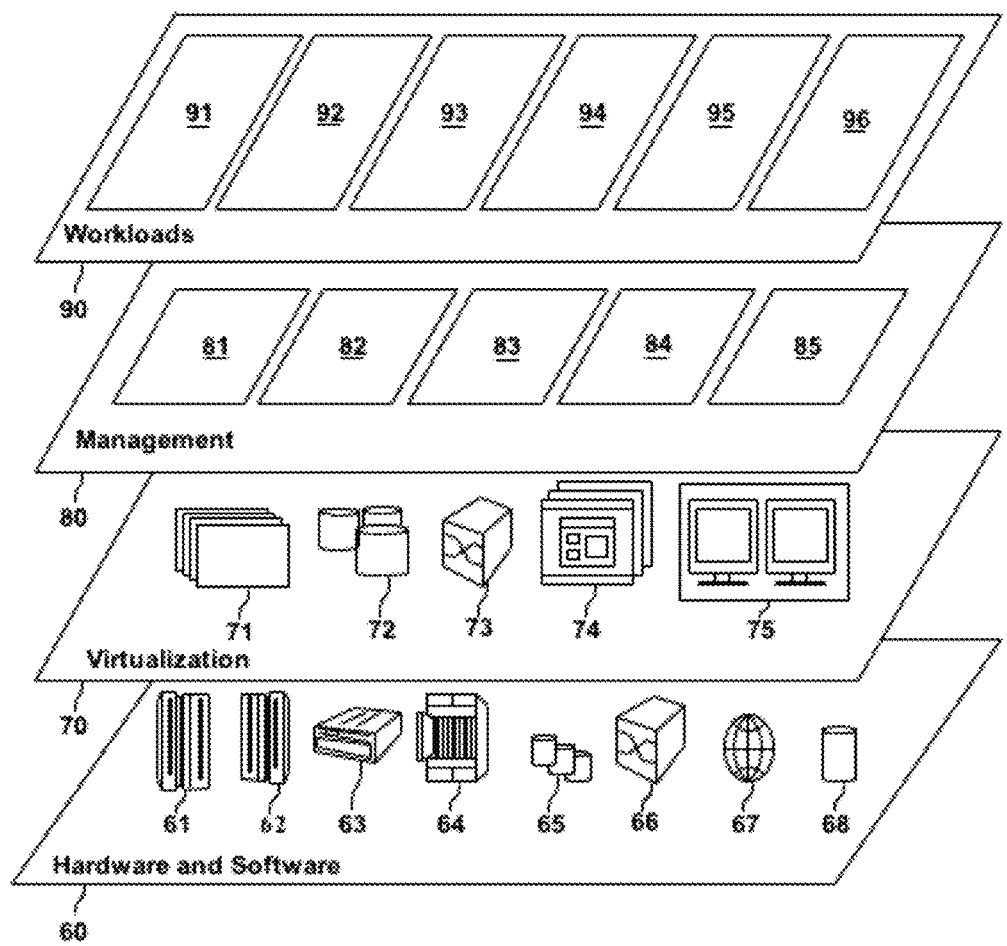
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and secure payment 96 according to embodiments of the invention.

Figure 4:
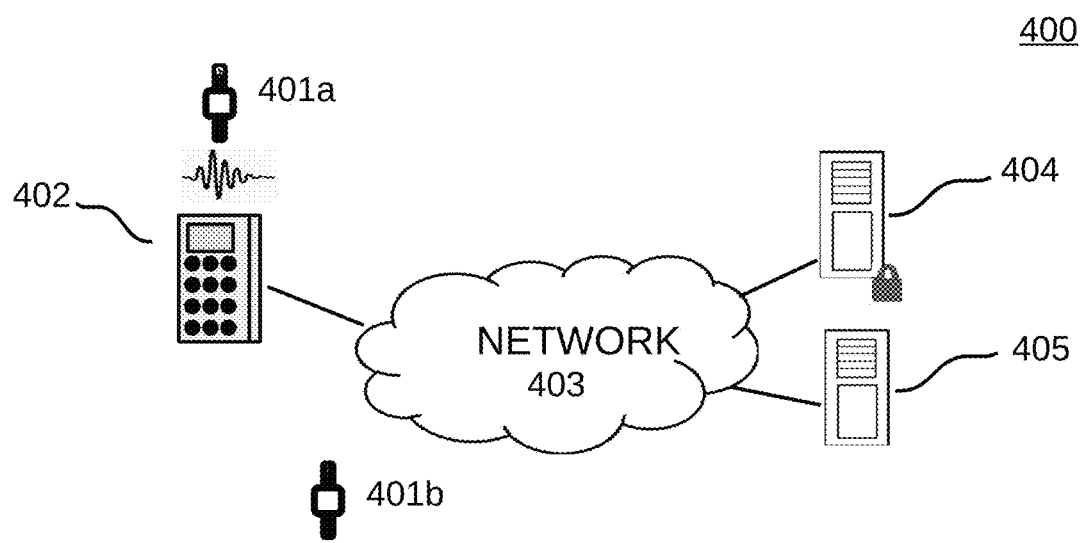
FIG. 4 illustrates a block diagram of an illustrative system in which embodiments of the present invention can be implemented.

FIG. 4 depicts an illustrative system diagram in which embodiments of the present invention can be implemented. As shown in FIG. 4, a point-of-sale (POS) device 402 can be connected to an authentication server 404 and a transaction server 405 via a network 403. Wearables 401a, 401b can directly connect to the authentication server 404 and the transaction server 405 via the network 403 or alternatively, via the POS device 402 and the network 403. The wearables 401a, 401b can be associated with different users (not shown). The authentication server 404 may be configured to verify the users and the transaction server 405 can be configured to complete transactions initiated by one of the users. Although it is shown in FIG. 4 that the authentication server 404 and the transaction server 405 are different servers, they can be one server with respect corresponding functionalities of the two different servers integrated within according to an embodiment of the invention. Although it is shown in FIG. 4 that the POS device 402 and authentication server 404 are different devices, they can be one device with respect corresponding functionalities of the two different devices integrated within according to an embodiment of the invention. The POS device 402, the authentication server 404 and the transaction server 405 can include internal and external hardware components as depicted in detail in the above with reference to FIG. 1. In other embodiments, the POS device 402, the authentication server 404 and the transaction server 405 can represent a cloud computing environment as described in relation to FIG. 2 in the above.

Figure 5:
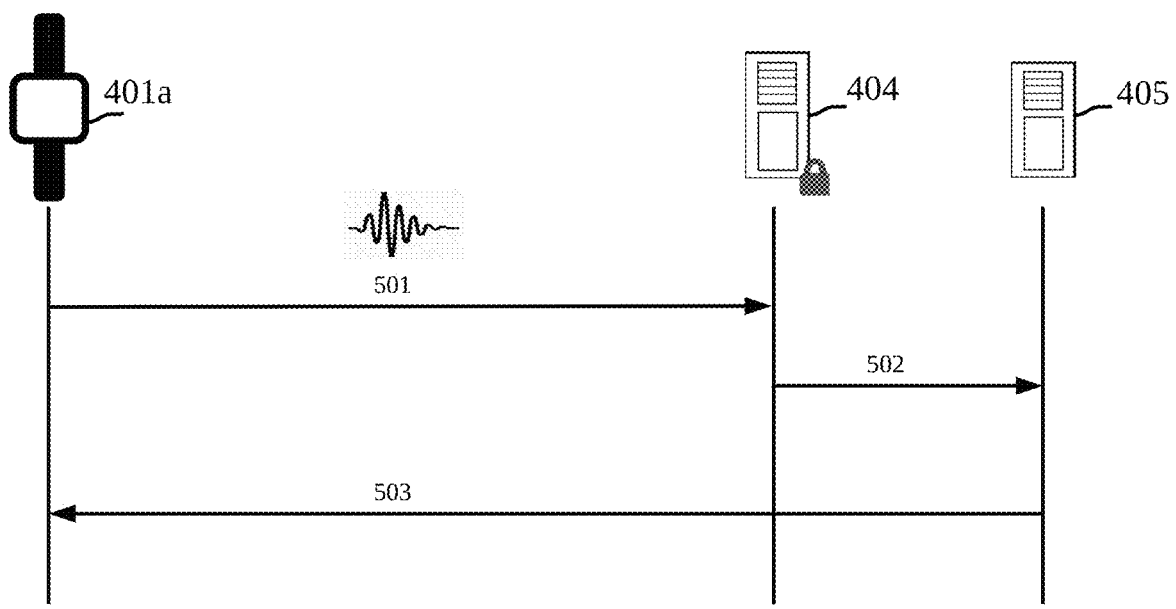
FIG. 5 illustrates an exemplary signal flow diagram according to an embodiment of the present invention.
Figure 6:
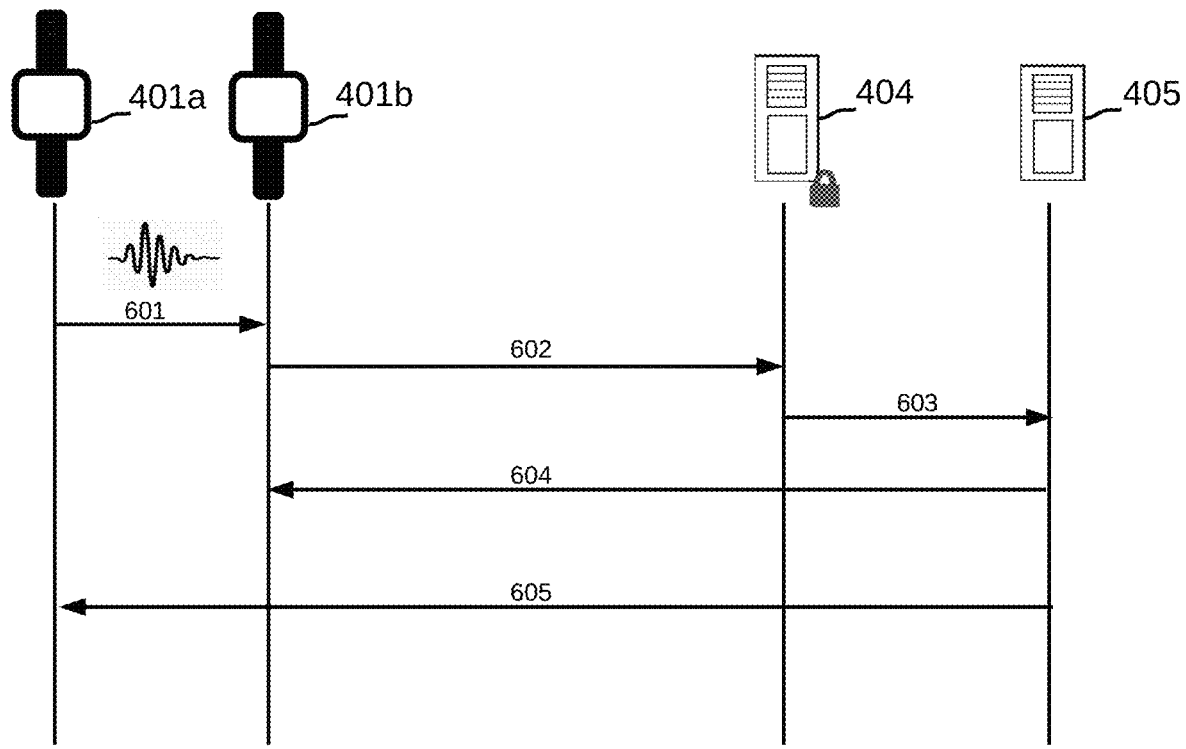
FIG. 6 illustrates an exemplary signal flow diagram according to another embodiment of the present invention.
Figure 7:
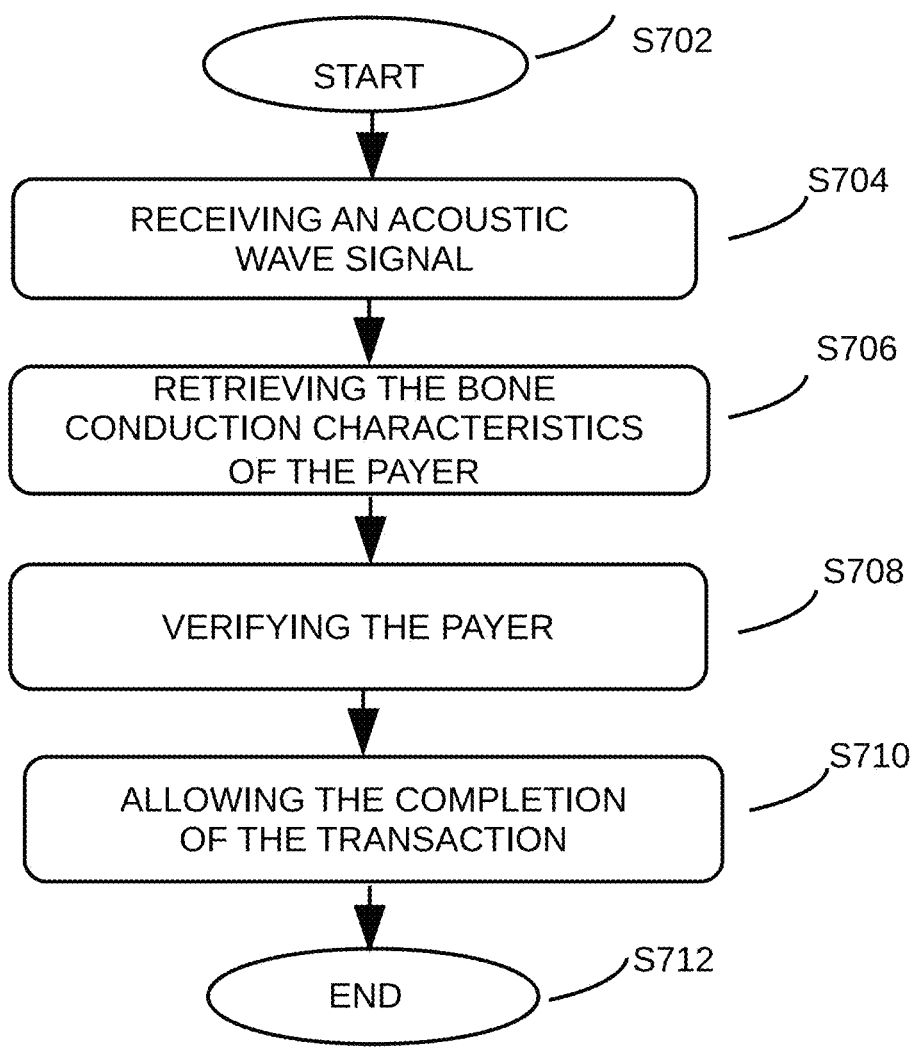
FIG. 7 illustrates a flowchart of an exemplary method according to an embodiment of the present invention.
Figure 8:
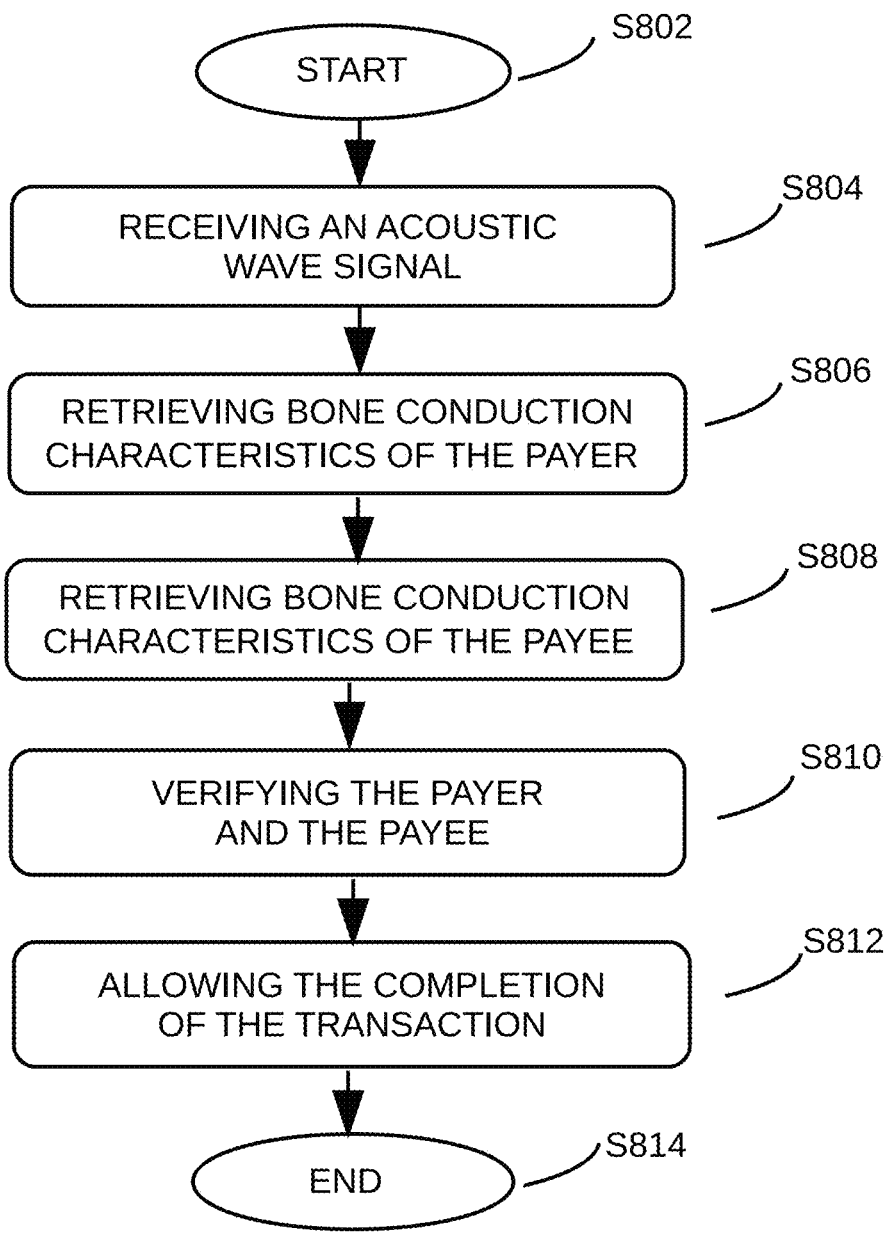
FIG. 8 illustrates a flowchart of an exemplary method according to another embodiment of the present invention.

In the following, embodiments of the present invention will be discussed in detail with references to FIG. 5 to FIG. 8 in which FIGS. 5 and 6 depict exemplary signal flow diagrams and FIG. 7 and FIG. 8 depict flow charts of exemplary methods according to various embodiments of the invention.

Now referring to FIG. 5, an exemplary signal flow diagram is illustrated according to an embodiment of the invention where a payer (not shown) can start a transaction utilizing a wearable 401a that a user wears by sending an acoustic wave signal 501 to an authentication server 404. According to an embodiment of the invention, the acoustic wave signal is based on a pre-determined carrier signal known to both the user and the authentication server 404. According to another embodiment of the invention, the pre-determined carrier signal is selected from a list of pre-determined signals and the selection is communicated to the authentication server 404. According to an embodiment of the invention, the acoustic wave signal is encoded with an identifier of the payer and transaction information of the transaction. According to an embodiment of the invention, the acoustic wave signal can be segmented into a plurality of sections with the identifier of the payer and the transaction information encoded in different sections respectively. Existing techniques can be utilized to segment the acoustic wave signal and to encode the identifier of the payer and the transaction information, for example, adding a space marker between two adjacent segments, and utilizing amplitude or frequency shift keying, etc.

Then, the acoustic wave signal 501 of the payer can be received directly by the authentication server 404, or via a POS device 402. According to an embodiment of the invention, the acoustic wave signal is converted from analog signal to digital signal by an Analog-Digital (AD) converter located within the POS device 402 before sending to the authentication server 404 in the case that the POS device 402 is presented between the wearable 401a and the authentication server 404.

Upon receiving the acoustic wave signal of the payer, the authentication server 404 decodes the acoustic wave signal 501 and obtains the identifier of the payer as well as the transaction information, by using the pre-determined carrier signal. According to an embodiment of the invention, the acoustic wave signal 501 can first be converted from analog signal to digital signal by an Analog-Digital (AD) converter located within the authentication server 404 in the case that the authentication server 404 receives the acoustic wave signal 501 in an analog form from the POS 402. The authentication server 404 can then retrieve a bone conduction characteristic of the payer from a database or a dedicated database server (not shown) connected to the authentication server 404 based on the identifier of the payer. Like fingerprints, irises, and brainwaves, bone conduction characteristics are other types of biometric characters of people that can be used to authenticate a person. A bone conduction characteristic of a person typically includes the characteristic frequency response of the person's bone, which is unique to the person. According to the invention, the bone conduction characteristic of the payer can be stored in the database or the database server in advance.

The authentication server 404 can then verify the payer based on the retrieved bone conduction characteristic of the payer. According to an embodiment of the invention, the authentication server 404 can generate an expected acoustic wave signal utilizing the identifier of the payer, the pre-determined carrier signal and the retrieved bone conduction characteristic of the payer. The expected acoustic wave signal is generated with the identifier of the payer as encoded information, the pre-determined carrier signal as the carrier, the bone conduction characteristic of the payer as the characteristics of the transmission media. The generation of the expected acoustic wave signal can utilize any existing techniques. Then the received acoustic wave signal and the expected acoustic wave signal are compared. If the comparison indicates a match, the payer is verified. The comparison of the expected acoustic wave signal and the received acoustic wave signal can utilize any existing techniques. The authentication server 404 can then allow the completion of the transaction by sending the decoded transaction information 502 to a transaction server 405 in response to the payer being verified. The transaction server 405 can then send to the payer a success message 503 after the transaction is successfully conducted or a failure message 503 if the transaction fails to conduct due to various reasons (for example, insufficient balance). If the comparison indicates a mismatch, the payer is not verified, further processing will be dropped. The authentication server 404 can then send to the payer a failure message (not shown).

Illustratively, the payer can be represented as $ID_1$, the transaction information can be represented as $TR_1$, the pre-determined carrier signal can be represented as $C_1$, and the bone conduction characteristic of the payer can be represented as $B_1$. The acoustic wave signal sent by the payer can be represented as:

$$W_S = B_1 C_1(ID_1) + B_1 C_1(TR_1) \qquad (1)$$

in which $W_S$ represents the acoustic wave signal 501 received by the authentication server 404, as the pre-determined carrier signal $C_1$ with the encoded information (the identifier of payer and the transaction information) will be propagated through the bone of the payer thus influenced by the bone conduction characteristic $B_1$.

The expected wave signal generated by the authentication server 404 can be represented as:

$$W_E = B'_1 C_1(ID_1) \qquad (2)$$

in which $W_E$ represents the expected acoustic wave signal generated by the authentication server 404, $B'_1$ represents the retrieved bone conduction characteristic of the payer, and $C_1$ represents the predetermined acoustic wave signal. If a section of the acoustic wave signal received by the authentication server 404, e.g., the section $B_1 C_1(ID_1)$ matches the expected acoustic wave signal generated by the authentication server 404, the payer is verified as it indicates the bone conduction characteristic $B_1$ of the payer who sends the acoustic wave signal matches the retrieved bone conduction characteristic $B'_1$ of the payer.

In the above, the signal flow according to an embodiment of the invention is described in detail. Although the acoustic wave signal described above is being transmitted and processed in analog form, it should be clear to those skilled in the art that the acoustic wave signal can also be transmitted and processed in digital form, which will also fall into embodiments of the invention.

FIG. 6 illustrates an exemplary signal flow diagram according to another embodiment of the present invention where a payer (not shown) can start a transaction utilizing a wearable 401a the user wears by sending an initial acoustic wave signal 601 to a wearable 401b of a payee (not shown). The initial acoustic wave signal 601 can have the identifier of the payer and transaction information of the transaction encoded, similar to the embodiment of FIG. 5. The payee can send an updated acoustic wave signal 602 to the authentication server 404 with the identifier of the payee added to the acoustic wave signal after receiving the initial acoustic wave signal 601 sent by the payer. According to an embodiment of the invention, the updated acoustic wave signal 602 can be segmented into a plurality of sections with the identifier of the payer, the identifier of the payee and the transaction information encoded in different sections. According to an embodiment of the invention, the acoustic wave signal is based on a pre-determined carrier signal known to both the user and the authentication server 404. According to another embodiment of the invention, the pre-determined carrier signal is selected from a list of pre-determined signals and the selection is communicated to the authentication server 404.

Upon receiving the updated acoustic wave signal from the payee, the authentication server 404 decodes the updated acoustic wave signal to obtain the identifier of the payer, the identifier of the payee, and the transaction information, using the pre-determined signal. The authentication server 404 can then retrieve a bone conduction characteristic of the payer associated with the identifier of the payer and a bone conduction characteristic of the payee associated with the identifier of the payee from a database or a dedicate database server (not shown) connected to the authentication server 404. The authentication server 404 can then verify the payer and the payee in the meantime based on the retrieved bone conduction characteristic of the payer and the retrieved bone conduction characteristic of the payee. According to an embodiment of the invention, the authentication server 404 can generate an expected acoustic wave signal utilizing the decoded identifier of the payer and the retrieved bone conduction characteristic of the payer, the decoded identifier of the payee and the retrieved bone conduction characteristic of the payee together with the pre-determined carrier signal as the carrier. The expected acoustic wave signal is generated with the identifier of the payer and the identifier of the payee as the encoded information, the pre-determined carrier signal as the carrier, the bone conduction characteristic of the payer and the bone conduction characteristic of the payee as the characteristics of the transmission media. Then section(s) of the received acoustic wave signal related to the identifier of the payer and the identifier of the payee and the expected acoustic wave signal are compared. If the comparison indicates a match, both the payer and the payee are verified. The authentication server 404 can then allow the completion of the transaction by sending the decoded transaction information 603 to a transaction server 405. The transaction server 405 can then send to the payer and the payee a success message 503 after the transaction is successfully conducted or a failure message 605 if the transaction fails to conduct due to various reasons (for example, insufficient balance). If the comparison indicates a mismatch, the payer or the payee is not verified, further processing will be dropped. The authentication server 404 can then send to the payer and the payee a failure message (not shown).

Illustratively, the payer can be represented as $ID_1$, the transaction information can be represented as $TR_1$, the pre-determined carrier signal can be represented as $C_1$, and the bone conduction characteristic of the payer can be represented as $B_1$, the payee can be represented as $ID_2$, and the bone conduction characteristic of the payee can be represented as $B_2$. The initial acoustic wave signal sent by the payer can be represented as:

$$W_S = B_1 C_1(ID_1) + B_1 C_1(TR_1) \tag{3}$$

in which $W_S$ represents the acoustic wave signal received by the payee, as the pre-determined carrier signal $C_1$ with the encoded information (the identifier of the payer and the transaction information) will be propagated through the bone of the payer thus influenced by the bone conduction characteristic $B_1$.

The updated acoustic wave signal sent by the payee can be represented as:

$$W'_S = B_2 B_1 C_1(ID_1) + B_2 B_1 C_1(ID_2) + B_2 B_1 C_1(TR_1) \tag{4}$$

in which $W'_S$ represents the updated acoustic wave signal received by the authentication server 404, as the pre-determined carrier signal $C_1$ with the encoded information (the identifier of the payer and the transaction information) will be propagated through the bone of the payer thus influenced by the bone conduction characteristic $B_1$ of the payer, and then updated with the payee and propagated through the bone of the payee thus further influenced by the bone conduction characteristic $B_2$ of the payee.

The expected wave signal generated by the authentication server 404 can be represented as:

$$W'_E = B'_2 B'_1 C_1(ID_1) + B'_2 B'_1 C_1(ID_2) \tag{5}$$

in which $W'_E$ represents the expected acoustic wave signal generated by the authentication server 404, $B'_1$ represents the retrieved bone conduction characteristic of the payer, $B'_2$ represents the retrieved bone conduction characteristic of the payee, and $C_1$ represents the pre-determined signal. If the section(s) of the updated acoustic wave signal received by the authentication server 404 matches the expected acoustic wave signal generated by the authentication server 404, the payer and the payee are both verified as it indicates the combination of the bone conduction characteristic $B_1$ of the payer and the bone conduction characteristic of the payee $B_2$ matches the combination of the retrieved bone conduction characteristic $B_1'$ of the payer and the bone conduction characteristic of the payee $B'_2$. As discussed above, the generation of expected wave signal $W_E$ and $W'_E$ can adopt any existing technologies.

FIG. 7 illustrates a flowchart of an exemplary method 700 according to an embodiment of the present invention. The method 700 starts at step S702 and proceeds to step S704, in which an acoustic wave signal is received. The acoustic wave signal can be encoded with an identifier of a payer of a transaction and transaction information of the transaction and based on a pre-determined carrier signal. Then at step S706, a bone conduction characteristic of the payer is retrieved based on the identifier of the payer. Both the identifier of the payer and the transaction information can be obtained from the acoustic wave signal for example by decoding the acoustic wave signal. Then at step S708, the payer is verified based on the retrieved bone conduction characteristic of the payer. Then, at step S710, the completion of the transaction is allowed based on the transaction information in responsive to the payer being verified. The method 700 then proceeds to step S712 and ends.

FIG. 8 illustrates a flowchart of an exemplary method 800 according to an embodiment of the present invention. The method 800 starts at step S802 and proceeds to step S804, in which an acoustic wave signal is received. The acoustic wave signal can be encoded with an identifier of a payer of the transaction, the identifier of a payee of the transaction and transaction information of the transaction and based on a pre-determined carrier signal. Then at step S806, a bone conduction characteristic of the payer is retrieved based on the identifier of the payer. Then at step S808, a bone conduction characteristic of the payee is retrieved based on the identifier of the payee. Both the identifier of the payer, the identifier of the payee, and the transaction information can be obtained from the acoustic wave signal for example by decoding the acoustic wave signal. Then, at step S810, the payer and the payee can be verified based on the retrieved bone conduction characteristic of the payer and the retrieved bone conduction characteristic of the payee. Then, at step S812, the completion of the transaction is allowed based on the transaction information in response to the payer and the payee being both verified. The method 800 then proceeds to step S814 and ends.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for securely performing electronic transactions over a network, comprising:
    receiving, by one or more processing units operatively coupled to a memory, a received acoustic wave signal propagated through a body of a payer, the received acoustic wave signal including a pre-determined carrier signal encoded with at least an identifier of the payer of a transaction and transaction information of the transaction, the received acoustic wave signal being generated by a computing device associated with the payer;
    obtaining, by the one or more processing units, the identifier of the payer and the transaction information from the received acoustic wave signal;
    retrieving, by the one or more processing units, a bone conduction characteristic of the payer from a database based on the identifier of the payer;
    generating, by the one or more processing units, an expected acoustic wave signal encoded with at least the identifier of the payer obtained from the received acoustic wave signal based on the bone conduction characteristic of the payer and converting the received acoustic wave signal from an analog signal to a digital signal for authentication; and
    allowing, by the one or more processing units, completion of the transaction based on the transaction information, including verifying the payer based on a comparison of the digital signal generated by the converting of the received acoustic wave signal with the expected acoustic wave signal indicating a match.

2. The method of claim 1, wherein the verification of the payer further comprises comparing at least one section of the received acoustic wave signal with the identifier of the payer encoded to the expected acoustic wave signal.

3. The method of claim 1, wherein the received acoustic wave signal is further encoded with an identifier of a payee of the transaction, and further comprising:
    obtaining the identifier of the payee from the received acoustic wave signal;
    retrieving a bone conduction characteristic of the payee based on the identifier of the payee; and
    allowing the completion of the transaction further based on the bone conduction characteristic of the payee.

4. The method of claim 3, wherein the expected acoustic wave signal is further encoded with the identifier of the payee obtained from the received acoustic wave signal based on the bone conduction characteristic of the payee; and
    the verification of the payer further comprises comparing at least one of the received acoustic wave signal with the identifier of the payer and the identifier of the payee encoded to the expected acoustic wave signal.

5. The method of claim 1, wherein the received acoustic wave signal is segmented into a plurality of sections and the identifier of the payer and the transaction information are encoded in respective ones of the sections.

6. A computer program product comprising a computer readable storage medium having a computer readable program stored therein, wherein the computer readable program, when executed on a computing device, causes the computing device to perform a method for securely performing electronic transactions over a network, the method comprising:
    receiving a received acoustic wave signal propagated through a body of a payer, the received acoustic wave signal including a pre-determined carrier signal encoded with at least an identifier of a payer of a transaction and transaction information of the transaction, the received acoustic wave signal being generated by a computing device associated with the payer;
    obtaining the identifier of the payer and the transaction information from the received acoustic wave signal;
    retrieving a bone conduction characteristic of the payer from a database based on the identifier of the payer;
    generating an expected acoustic wave signal encoded with at least the identifier of the payer obtained from the received acoustic wave signal based on the bone conduction characteristic of the payer and converting the received acoustic wave signal from an analog signal to a digital signal for a authentication; and
    allowing completion of the transaction based on the transaction information, including verifying the payer based on a comparison of the digital signal generated by the converting of the received acoustic wave signal with the expected acoustic wave signal indicating a match.

7. The computer program product of claim 6, wherein the verification of the payer further comprises comparing at least one section of the received acoustic wave signal with the identifier of the payer encoded to the expected acoustic wave signal.

8. The computer program product of claim 6, wherein the received acoustic wave signal is further encoded with an identifier of a payee of the transaction, and wherein the method further comprises:
    obtaining the identifier of the payee from the received acoustic wave signal;

retrieving a bone conduction characteristic of the payee based on the identifier of the payee; and allowing the completion of the transaction further based on the bone conduction characteristic of the payee.

9. The computer program product of claim 8, wherein the expected acoustic wave signal is further encoded with the identifier of the payee obtained from the received acoustic wave signal based on the bone conduction characteristic of the payee; and the verification of the payer further comprises comparing at least one section of the received acoustic wave signal with the identifier of the payer and the identifier of the payee encoded to the expected acoustic wave signal.

10. The computer program product of claim 6, wherein the received acoustic wave signal is segmented into a plurality of sections and the identifier of the payer and the transaction information are encoded in respective ones of the sections.

11. The method of claim 1, wherein the computing device associated with the payer includes a wearable device.

12. The computer program product of claim 6, wherein the computing device associated with the payer includes a wearable device.

13. A computer-implemented method for securely performing electronic transactions over a network, comprising:

generating, by a computing device of a payer, a payer acoustic wave signal, the payer acoustic wave signal including a pre-determined carrier signal encoded with at least an identifier of the payer of a transaction and transaction information;

propagating the payer acoustic wave signal through a body of the payer;

receiving, by one or more processing units operatively coupled to a memory, the payer acoustic wave signal propagated through a body of the payer;

obtaining, by the one or more processing units, the identifier of the payer and the transaction information from the acoustic wave signal;

retrieving, by the one or more processing units, a bone conduction characteristic of the payer from a database based on the identifier of the payer;

generating, by the one or more processing units, an expected acoustic wave signal, the expected acoustic wave signal including the pre-determined carrier signal encoded with at least the identifier of the payer based on the bone conduction characteristic of the payer and converting the received acoustic wave signal from an analog signal to a digital signal for authentication; and allowing, by the one or more processing units, completion of the transaction based on the transaction information, including verifying the payer based on a comparison of the digital signal generated by the converting of the payer acoustic wave signal with the expected acoustic wave signal indicating a match.

* * * * *